US011850595B2

(12) United States Patent
Leslie et al.

(10) Patent No.: US 11,850,595 B2
(45) Date of Patent: Dec. 26, 2023

(54) NANOFLUIDIC FLOW CELL AND METHOD OF LOADING SAME

(71) Applicant: THE ROYAL INSTITUTION FOR THE ADVANCEMENT OF LEARNING/MCGILL UNIVERSITY, Montréal (CA)

(72) Inventors: Sabrina Rose Leslie, Montréal (CA); François Michaud, Montréal (CA); Daniel James Berard, Montréal (CA); Gilead Henkin, Montréal (CA); Albert Kamanzi, Montréal (CA)

(73) Assignee: The Royal Institution for the Advancement of ..., Montreal (CA)

( * ) Notice: Subject to any disclaimer, the term of this patent is extended or adjusted under 35 U.S.C. 154(b) by 430 days.

(21) Appl. No.: 17/112,297

(22) Filed: Dec. 4, 2020

(65) Prior Publication Data
US 2021/0114030 A1    Apr. 22, 2021

Related U.S. Application Data

(63) Continuation-in-part of application No. 15/654,339, filed on Jul. 19, 2017, now abandoned.
(Continued)

(51) Int. Cl.
*B81B 1/00* (2006.01)
*B01L 3/00* (2006.01)

(52) U.S. Cl.
CPC . *B01L 3/502761* (2013.01); *B01L 2200/0668* (2013.01); *B01L 2300/0681* (2013.01);
(Continued)

(58) Field of Classification Search
None
See application file for complete search history.

(56) References Cited

U.S. PATENT DOCUMENTS

| 7,169,251 | B2 | 1/2007 | Guo et al. | |
|---|---|---|---|---|
| 2002/0185184 | A1* | 12/2002 | O'Connor | B01F 33/30 137/822 |

(Continued)

OTHER PUBLICATIONS

Shoura Massa J. et al., Measurements of DNA-Loop Formation via Cre-Mediated Recombination; Nucleic Acids Res. vol. 40, pp. 7452-7464, 2012.
(Continued)

*Primary Examiner* — Paul S Hyun
(74) *Attorney, Agent, or Firm* — FASKEN MARTINEAU DUMOULIN LLP; Serge Lapointe

(57) ABSTRACT

A flow cell for confining molecules in a fluid. The flow cell includes an upper substrate, an upper support member, a center substrate, a membrane, a lower support member and a lower substrate. The lower support member comprises an imaging chamber it is positioned below the membrane and above the lower substrate. In one embodiment the membrane comprises a nanopore and nanoscale groove extending through the membrane. In another embodiment the lower substrate comprises an upper face in communication with the imaging chamber, and the upper face comprises a plurality of nanoscale grooves extending partially through the lower substrate. In both embodiments the upper substrate, upper support member, center substrate and membrane are displaceable through the imaging chamber, thereby causing molecules in the imaging chamber to be confined or trapped through the nanoscale groove(s) of the membrane or of the lower substrate.

18 Claims, 12 Drawing Sheets

Related U.S. Application Data

(60) Provisional application No. 62/364,359, filed on Jul. 20, 2016.

(52) U.S. Cl.
CPC .............. *B01L 2300/0816* (2013.01); *B01L 2300/0893* (2013.01); *B01L 2300/0896* (2013.01)

(56) References Cited

U.S. PATENT DOCUMENTS

| | | |
|---|---|---|
| 2004/0029101 A1 | 2/2004 | Orwar et al. |
| 2013/0072386 A1 | 3/2013 | Xiao et al. |
| 2013/0170026 A1 | 7/2013 | Cohen et al. |
| 2014/0332098 A1 | 11/2014 | Juncker et al. |
| 2017/0160188 A1 | 6/2017 | Cohen et al. |

OTHER PUBLICATIONS

Leslie Sabrina R. et al.; Convex Lens-Induced Nanoscale Templating; Proc. Natl. Acad. Sci. vol. 111, 13295, 2014.
Henkin Gil et al.; Manipulating and Visualizing Molecular Interactions in Customized Nanoscale Spaces; Analytical Chemistry, 88 (22), 11100-11107(2016).
Berard Daniel J. et al.; Formatting and ligating biopolymers using adjustable nanoconfinement; Appl. Phys. Lett. 109, 033702 (2016).
Ahamed Mohammed Jalal et al.; Continuous Confinement Fluidics: Getting Lots of Molecules in Small Spaces; Macromolecules 49, (7) 2853-285 (2016).
Berard Daniel et al; Precision Platform for Convex Lens-Induced Confinement Microscopy; Rev. Sci. Instrum. 84, 103704 (2013).
Elting Mary W. et al.; Single-molecule fluorescence imaging of processive myosin with enhanced background suppression using linear Zero Mode Waveguides (ZMW) and Convex Lens-induced Confinement (CLIC)—Optics Express 21 (1), 1189-1202 (2013).
Leslie Sabrina R.; Convex Lens-induced Confinement for Imaging Single Molecules—Analytical Chemistry 82 (14), 6224-6229 (2010).

\* cited by examiner

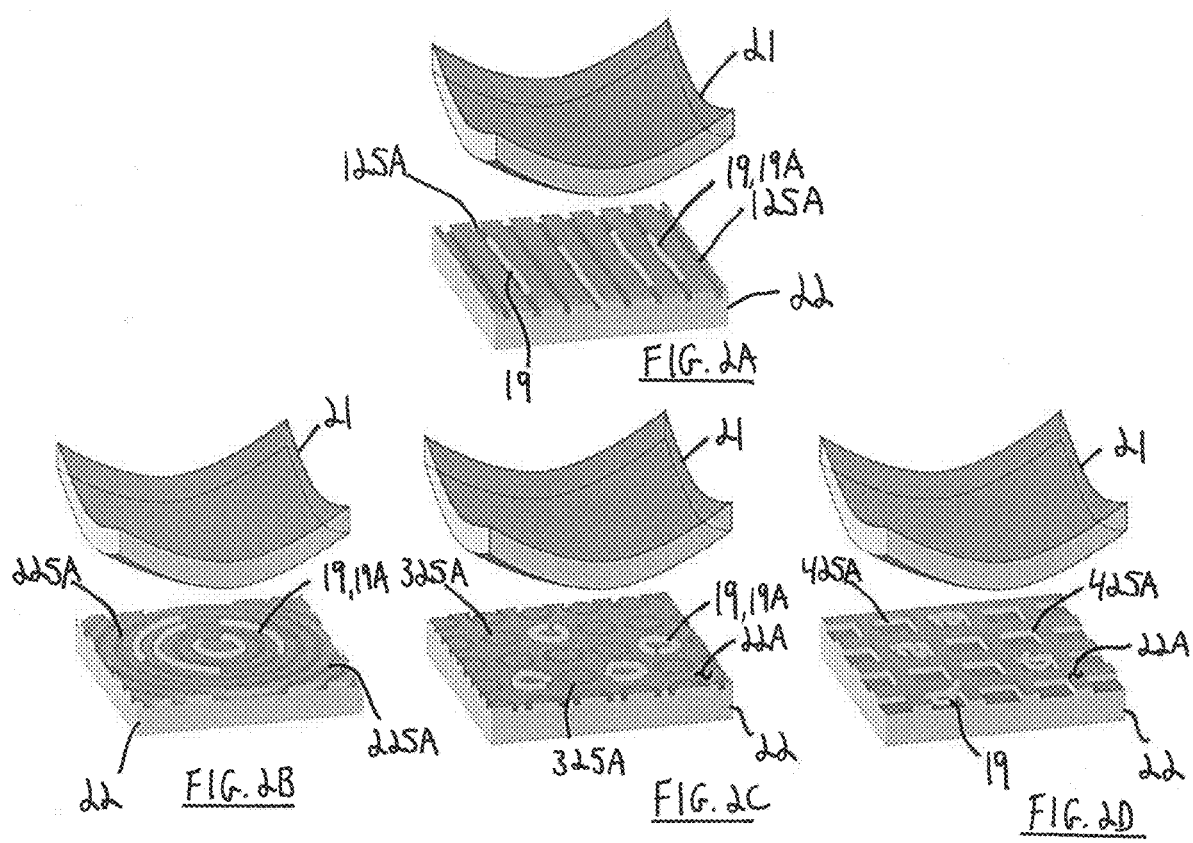
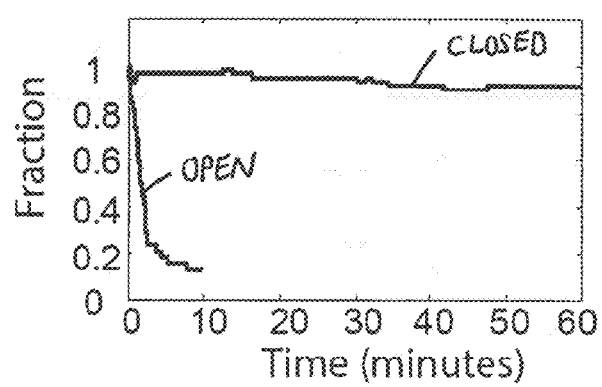
FIG. 2E

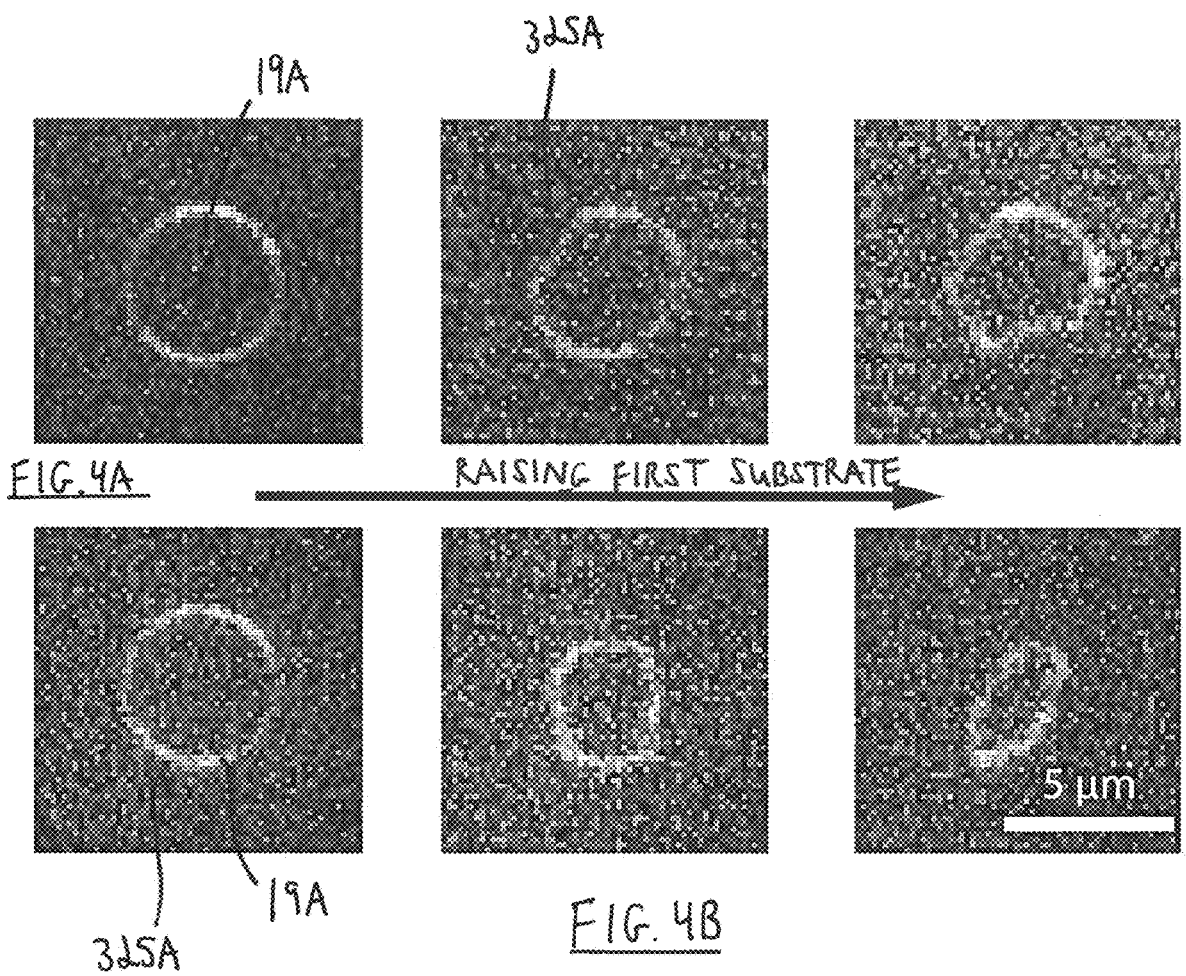

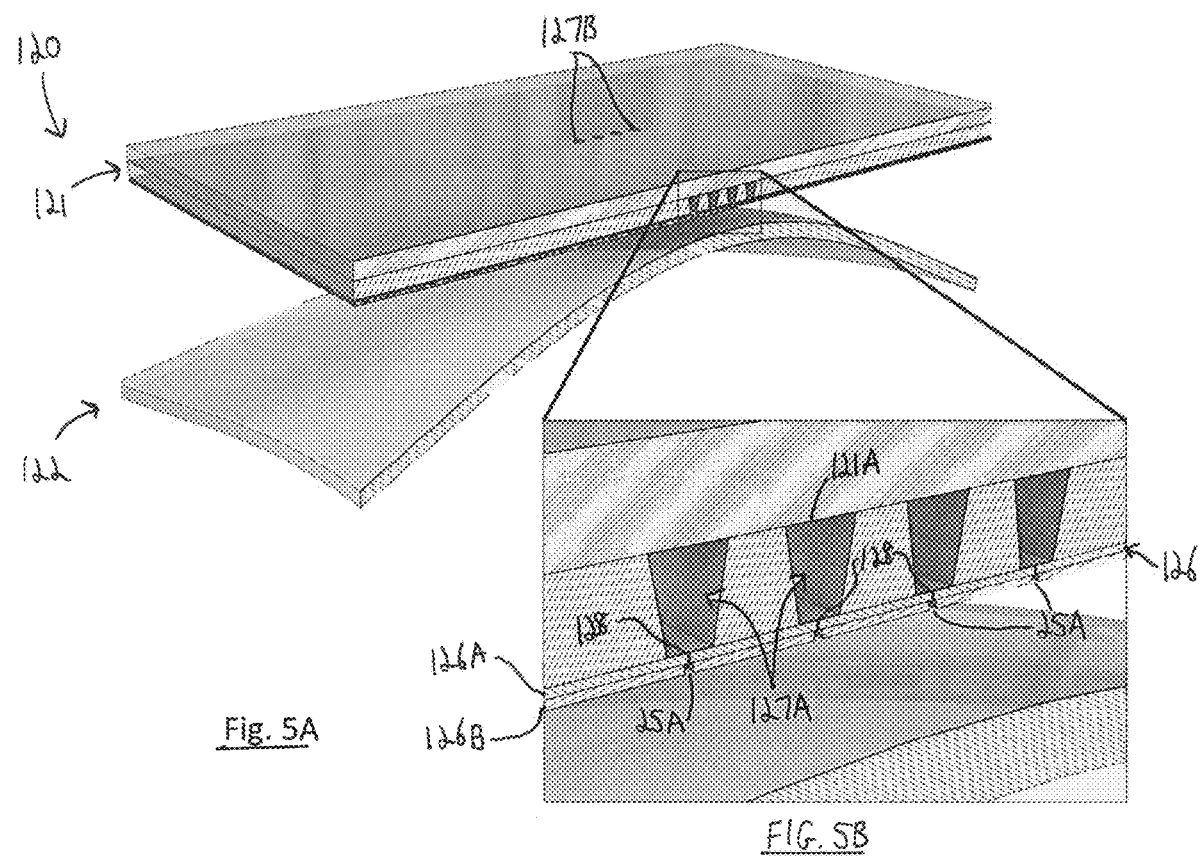
Fig. 5A
FIG. 5B
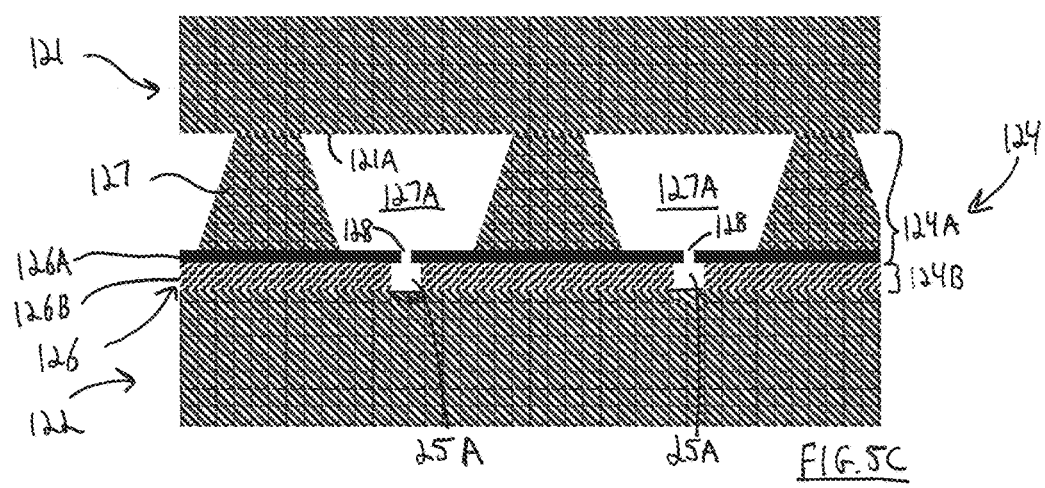
FIG. 5C

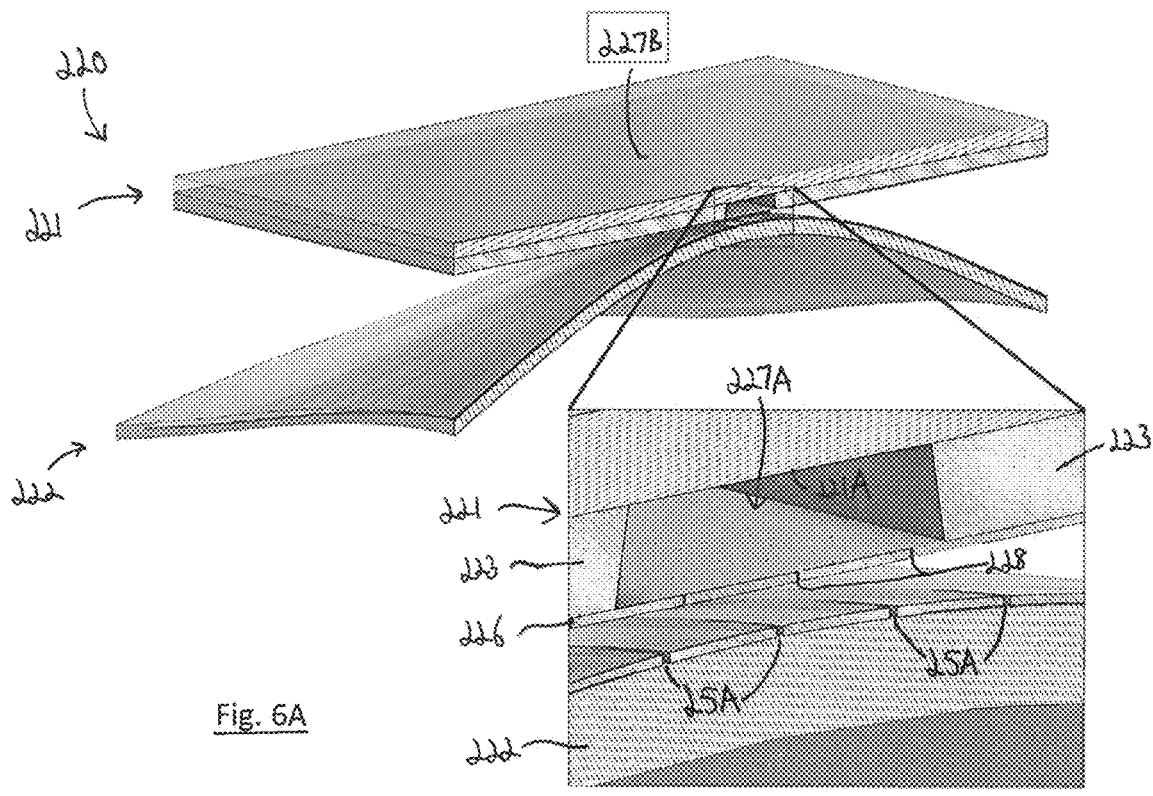
Fig. 6A
FIG. 6B
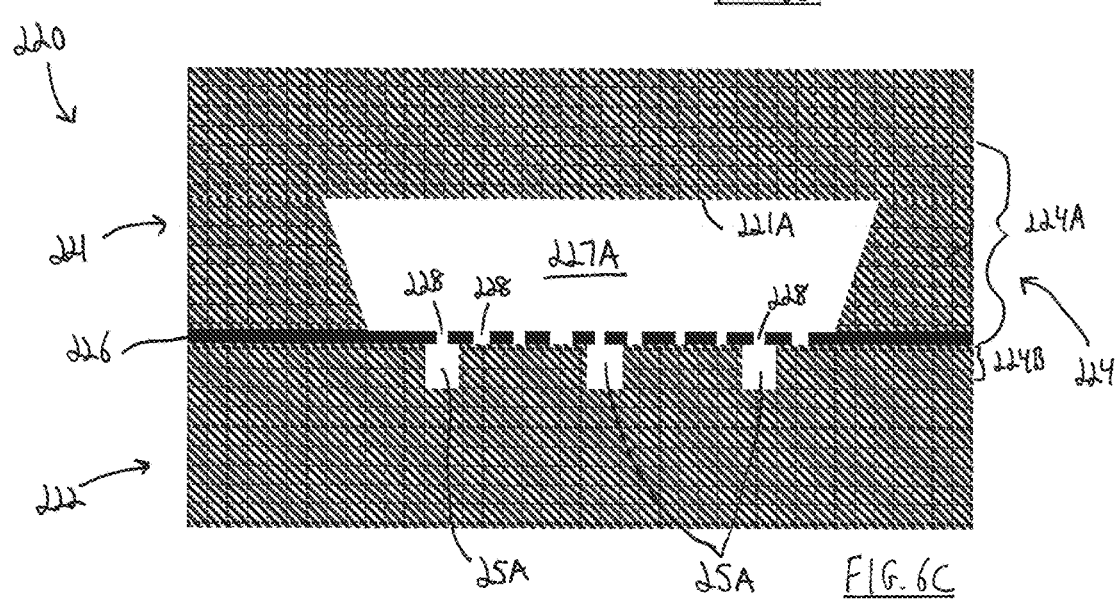
FIG. 6C

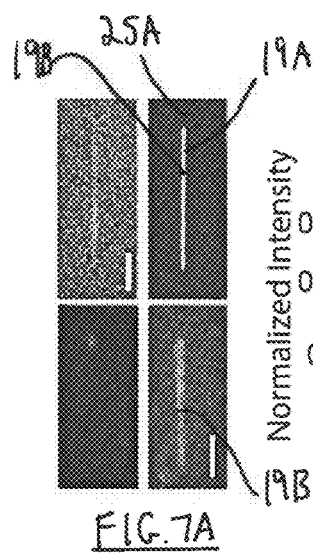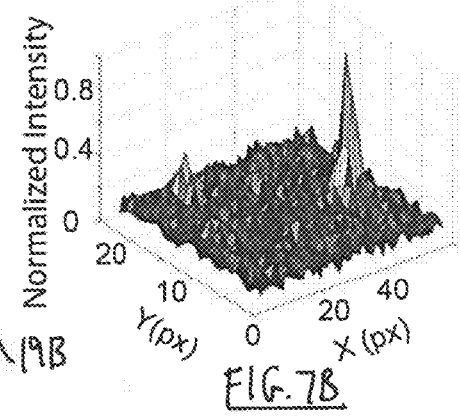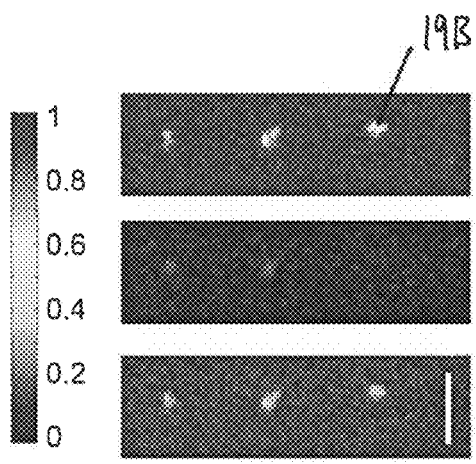
FIG. 7A  FIG. 7B  FIG. 7C
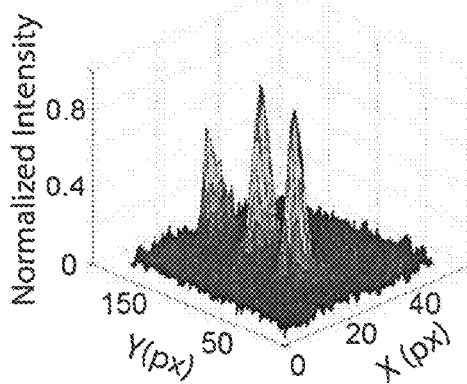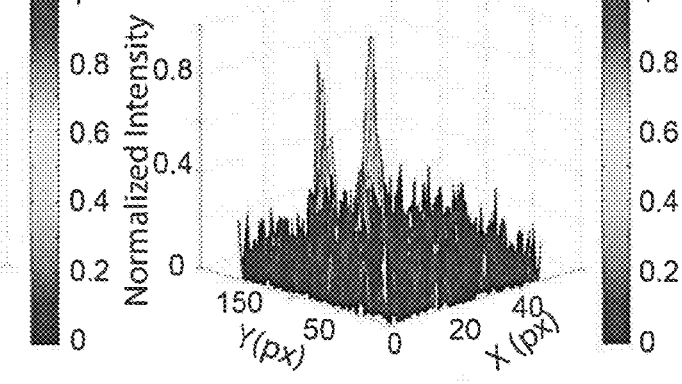
All scale bars are 5 μm
FIG. 7D  FIG. 7E

NANOFLUIDIC FLOW CELL AND METHOD OF LOADING SAME

CROSS-REFERENCE TO RELATED APPLICATIONS

[None]

TECHNICAL FIELD

The application relates generally to molecular analysis and, more particularly, to a flow cell for same.

BACKGROUND

The direct visualization, manipulation, and quantification of long, delicate biopolymers is a challenge faced by emerging biotechnologies. Establishing long-range structural information when analyzing genomic DNA, protein-DNA complexes, or other biopolymers can be limited by polymer breakage within devices during handling.

SUMMARY

In one aspect, there is provided a flow cell for confining molecules in a fluid, comprising: a first substrate and a second substrate being spaced apart by support members, the first and second substrates and the support members defining a fluidic chamber to receive the fluid, at least one of the first and second substrates having a nanoscale surface topography including at least one nanoscale groove, at least one of the first and second substrates being displaceable through the fluidic chamber to contact the first substrate against the second substrate, contact between the first substrate and the second substrate causing displacement of the molecules into the at least one nanoscale groove.

In another aspect, there is provided a method of loading a flow cell, comprising: providing molecules in a fluid between spaced-apart first and second substrates, at least one of the first and second substrates having a nanoscale surface topography including at least one nanoscale groove extending into said substrate; and displacing at least one of the first and second substrates to contact the first substrate against the second substrate, contact between the first substrate and the second substrate causing displacement of the molecules in the fluid into the at least one nanoscale groove and confining the molecules therein.

In a further aspect, there is provided a method of loading a flow cell, comprising: deforming at least part of the flow cell to confine a biological molecule within a nanoscale groove of the flow cell such that a first end of the biological molecule is proximate to a second end of the biological molecule.

DESCRIPTION OF THE DRAWINGS

Reference is now made to the accompanying figures in which:

FIG. 2A is a schematic view of a nanoscale surface topography on a substrate of a flow cell;

FIG. 2B is a schematic view of another nanoscale surface topography on a substrate of a flow cell;

FIG. 2C is a schematic view of yet another nanoscale surface topography on a substrate of a flow cell;

FIG. 2D is a schematic view of yet another nanoscale surface topography on a substrate of a flow cell;

FIG. 2E shows the fraction of the initial number of trapped DNA molecules in a single field of view plotted as a function of time for both open and closed nanoscale groove geometries;

FIGS. 4A and 4B show two ligation events of a DNA molecule within a ring-shaped nanoscale groove;

FIG. 5A is a perspective view of a flow cell according to yet another embodiment of the present disclosure, for use with the instrument of FIG. 1A;

FIG. 5B is an enlarged view of the outlined area of FIG. 5A;

FIG. 5C is a cross-sectional schematic view of the flow cell of FIG. 5A in a closed position;

FIG. 6A is a perspective view of a flow cell according to yet another embodiment of the present disclosure, for use with the instrument of FIG. 1A;

FIG. 6B is an enlarged view of the outlined area of FIG. 6A;

FIG. 6C is a cross-sectional schematic view of the flow cell of FIG. 6A in a closed position; and FIGS. 7A to 7E show two examples of a DNA molecule labeled with a single fluorophore extended in a linear nanoscale groove and trapped in an embedded micro-pit.

FIG. 11A is a perspective cross-sectional and transparent view of the whole flow cell; FIG. 11B is perspective cross-sectional enlarged view of a section of the flow cell of FIG. 11A that is bended during use; FIG. 11C is a cross-sectional enlarged view of a section of the flow cell of FIG. 11A; and FIG. 11D is a perspective cross-sectional enlarged view of a section of the flow cell of FIG. 11B.

FIG. 12A is a perspective cross-sectional and transparent view of the whole flow cell; FIG. 12B is perspective cross-sectional enlarged view of a section of the flow cell of FIG. 12A that is bended during use; FIG. 12C is a cross-sectional enlarged view of a section of the flow cell of FIG. 12A; and FIG. 12D is a perspective cross-sectional enlarged view of a section of the flow cell of FIG. 12B.

DETAILED DESCRIPTION

Figure 1A:
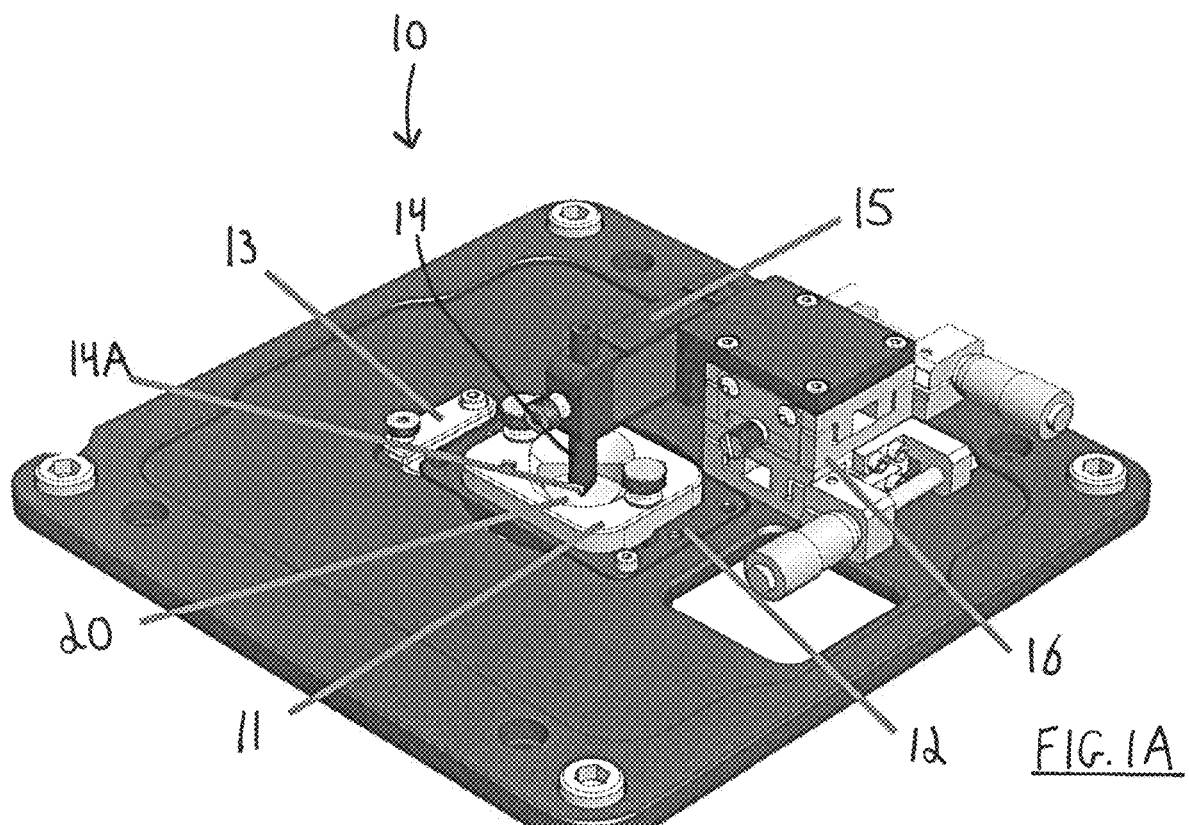
FIG. 1A is a perspective view of an instrument for a flow cell, according to an embodiment of the present disclosure.

FIG. 1A shows an instrument 10 for manipulating a nanofluidic flow cell 20. The instrument includes a microfluidic chuck 11 for receiving the flow cell 20. The chuck 11 is mounted to a sample holder 12, which is secured in place with a clamp 13. As will be described in greater detail below, various portions and components of the flow cell 20 can be displaced by the instrument 10 to analyse molecules within the flow cell 20. In the depicted embodiment, the instrument 10 has a deflection rod 14 having a rounded or pointed end 14A which presses against portions of the flow cell 20. Vertical displacement of the deflection rod 14 is controlled by a Z-axis piezoelectric actuator 15, which provides for 100 µm travel of the deflection rod 14 along the Z-axis. The vertical translation of the pointed end 14A of the deflection rod 14 brings it into contact with the top surface of the flow cell 20. The position of the deflection rod 14 on the X-Y plane of the instrument 10 is controlled by a horizontal micropositioner 16. The micropositioner 16 is operable to effect minute displacements in the X-Y plane, for example at the level of a micron, of the deflection rod 14 to align the deflection rod 14 with the portion of the flow cell 20 to be displaced.

Figure 1B:
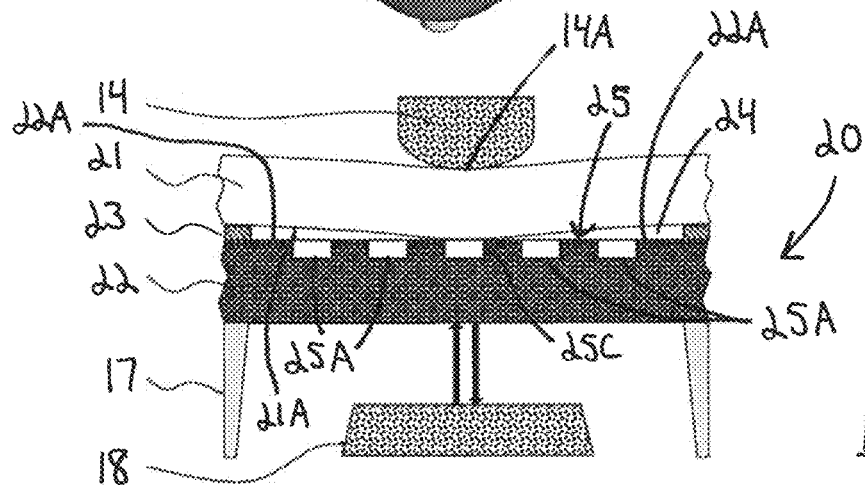
FIG. 1B is a cross-sectional schematic view of part of the instrument and flow cell of FIG. 1A.

FIG. 1B shows the flow cell 20, which in the depicted embodiment, is used for imaging molecules confined within the flow cell 20. The imaging technique in the depicted embodiment is optical microscopy, and more particularly, fluorescence microscopy. Since the flow cell 20 is used to displace and confine the molecules, as described in more detail below, it can be used for other molecular analysis or manipulation purposes. Non-limiting examples of other purposes include sequencing base pairs, enabling biomarker detection, and identifying and/or characterizing a biomolecule using larger-scale properties rather than single-base measurements. The flow cell 20 in the depicted embodiment is used to confine and analyse DNA molecules in a fluid solution. It will be appreciated that the flow cell 20 can be used to analyse or manipulate other molecules and biological molecules in a fluid solution, and is not limited to being used only with DNA molecules.

The flow cell 20 includes a first substrate 21 and a second substrate 22. One or both of the first and second substrates 21,22 has a surface upon structures on the scale of nanometers are formed in order to confine the molecules for analysis. The first and second substrates 21,22 are spaced apart by one or more support members 23. In the depicted embodiment, the support members 23 are the walls of the substrates 21,22. In an alternate embodiment, the support members 23 are spacers or posts.

The first and second substrates 21,22 and the support members 23 collectively define a fluidic chamber 24 for receiving the molecules. The first and second substrates 21,22 and the support members 23 define the boundaries of the fluidic chamber 24 and prevent the solution containing the molecules from leaking out. The fluidic chamber 24 is therefore a sealed chamber. The expression "fluidic chamber 24" refers to a volume or spaced defined by the structure of the flow cell 20 with typical characteristic dimensions within the range of 1-100 nm when its geometry is confined, as discussed in greater detail below. The fluidic chamber 24 and/or substrates 21,22 may include one or more inlets or outlets for admitting or releasing fluid from within the fluidic chamber 24.

Still referring to FIG. 1B, the second substrate 22 has a nanoscale surface topography 25. The nanoscale surface topography 25 is an arrangement of nanoscale structures on the second substrate 22. More particularly, the second substrate 22 is patterned with one or more nanoscale structures such that biological or other molecules can be "loaded" into the nanoscale structures and confined therein. A "nanoscale structure" refers to a structure having one or more dimensions at the nanometer level, which is typically between 0.1 nm and 100 nm. Examples of such nanoscale structures include, but are not limited to, textured surfaces having one dimension on the nanoscale, tubes having two dimensions on the nanoscale, and particles having three dimensions on the nanoscale. Examples of nanoscale textured surfaces include, but are not limited to, grooves, channels, pits, and ridges. Examples of nanoscale tubes include, but are not limited to, structures having geometries resembling tubes, solid rods, whiskers, and rhomboids with square, rectangular, circular, elliptical, and other polygonal cross-sections perpendicular to an axis of the tube. Examples of nanoscale particles include, but are not limited to, structures having geometries representing spheres, pyramids, and cubes. The cross-sectional geometry of nanoscale tubes and nanoscale particles may not be constant such that a nanoscale structure may taper in one or two dimensions. The flow cell 20 therefore has a nanoscale surface-embedded topography 25, or "NanoSET".

Nanoscale structures such as linear groove arrays, concentric circular grooves, rectangular wells, ring-shaped groove arrays, and pit arrays can be fabricated on 100 mm (4") diameter, 0.17 mm thick D263 borosilicate glass wafers forming the substrates 21,22. Examples of such features include $27 \times 27 \times 200,000$ $nm^3$ and $50 \times 50 \times 200,000$ $nm^3$ nanoscale channels, $50 \times 600 \times 600$ $nm^3$ and $50 \times 900 \times 900$ $nm^3$ nanoscale pits fabricated using electron-beam lithography and reactive ion etching (RIE). 1 µm deep microchannels connecting the nanoscale structures for fluidic coupling to the external microfluidic circuit can also be formed.

Figure 1C:
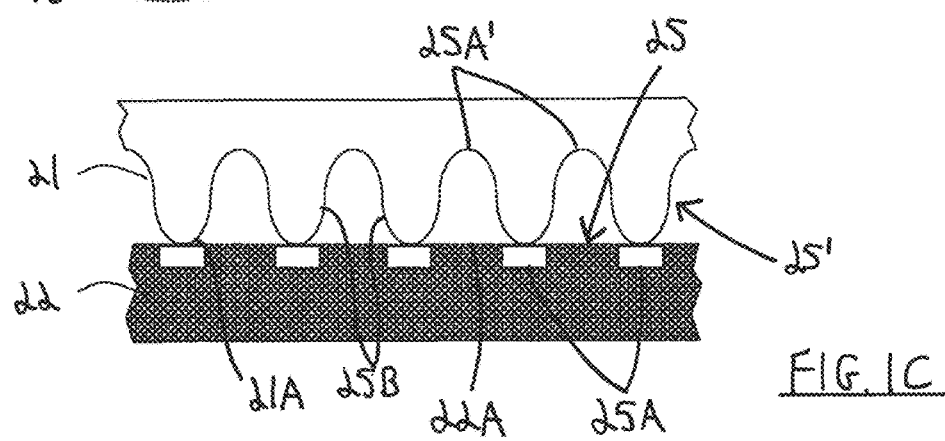
FIG. 1C is a cross-sectional schematic view of a flow cell according to another embodiment of the present disclosure, for use with the instrument of FIG. 1A.

In the embodiment of FIG. 1B, the nanoscale surface topography 25 includes multiple nanoscale grooves 25A that extend into the second substrate 22 from a surface 22A thereof. The fluidic chamber 24 includes the volume of the nanoscale grooves 25A. In the embodiment of FIG. 1C, both the first and the second substrate 21,22 have a nanoscale surface topography 25. The nanoscale surface topography 25 for the second substrate 22 includes multiple nanoscale grooves 25A that extend into the second substrate 22 from the surface 22A. The nanoscale surface topography 25' for the first substrate 21 also includes multiple nanoscale grooves 25A' that extend into the first substrate 21 from the surface 21A. The fluidic chamber 24 includes the volume of the nanoscale grooves 25A,25A'. The nanoscale grooves 25A' form nanoscale posts 25B extending outwardly from a recessed surface of the first substrate 21. In the depicted embodiment, each nanoscale post 25B has a height of 20 nm. Other heights and widths for the nanoscale posts 25B are possible. The nanoscale posts 25B help to create a nanoscale gap between the first and second substrates 21,22 when they are pressed together into stable contact.

In the embodiment of FIG. 1B, the first and second substrates 21,22 are two $25 \times 25$ $mm^2$ glass plates separated by a 10 µm vertical support member 23 around their edges. The first, or "upper", substrate 21 has two small inlet holes near the corners for fluid insertion into the fluidic chamber 24. The first substrate 21 forms a deformable lens to vary the fluidic chamber 24 by deforming the first glass substrate 21 using the pointed end 14A of the deflection rod 14. The first substrates 21 is shown as a convex lens, mounted curved face down. Supports 17 space the second, or "lower", substrate 22 from an illumination/viewing lens 18. In the depicted embodiment, the convex lens defined by the first substrate 21 becomes spherical when deformed, and the curved deformation of the first substrate 21 occurs along the Z-axis perpendicular to the length of the first substrate 21.

It will therefore be appreciated that one or both of the first and second substrates 21,22 is displaceable toward each other. Still referring to FIG. 1B, at least a central part of the first substrate 21 is displaceable by deformation caused by the displacement rod 14 to contact the part of the first substrate 21 against the second substrate 22. In an alternate embodiment, the first substrate 21 is displaced by translation toward the second substrate 22. It will be appreciated that the displacement of the first and second substrates 21,22 is a relative displacement, in that either one of the first and second substrates 21,22 can be displaced to provide contact between their surfaces 21A,22A. The effect of the displacement of the first substrate 21 is to cause the molecules in the fluid within the fluidic chamber 24 to be displaced toward the nanoscale grooves 25A and confined therein. More particularly, as the volume of the fluidic chamber 24 is decreased by the displacement of the first substrate 21 toward the second substrate 22, the molecules are increasingly urged towards the nanoscale grooves 25A until they remain trapped within the nanoscale grooves 25A by contact between the surfaces 21A,22A. The molecules when they are within the one or more nanoscale grooves 25A are trapped therein by the walls 25C of the nanoscale grooves 25A, and by the surface 21A of the first substrate 21. The size, and thus the volume, of the fluidic chamber 24 varies with the displacement of the first substrate 21. The fluidic chamber 24 before displacement of the first substrate has dimensions on the micron scale, or at least hundreds of nanometers, when the fluid is received therein. When the volume of the fluidic chamber 24 is decreased by displacement of the first substrate, the fluidic chamber 24 is squeezed to the nanoscale and made very thin. In such a squeezed configuration, the fluidic chamber 24 becomes a nanofluidic chamber.

An exemplary use of the flow cell 20 is now described, with reference to FIG. 1B. After the fluid solution containing the DNA molecules is added into the fluidic chamber 24, the pointed end 14A of the deflection rod 14 is lowered into contact with the top of the first substrate 21. Immersion oil can be used to prevent laser reflections between the lens of the instrument 10 and the first substrate 21. The first substrate 21 is deformed into contact with the second substrate 22 and the geometry of the fluidic chamber 24 is allowed to stabilize. Once the confinement level is high enough, the confinement of the DNA molecules within the nanoscale grooves 25A can be visually observed.

Different geometries of the nanoscale grooves 25A are shown in FIGS. 2A to 2D. In FIG. 2A, the second substrate 22 has multiple linear and open nanoscale grooves 125A which extend along an entire length of the second substrate 22. The nanoscale grooves 125A are said to be "open" because the movement of the molecules 19 therein is constrained only by the walls of the nanoscale grooves 125A that are parallel to the longitudinal axis of the nanoscale grooves 125A. Stated differently, the molecules 19 can exit each open nanoscale groove 125A at either one of its ends when the first substrate 21 is contacting the second substrate 22. Furthermore, the molecules' conformations can fluctuate in the vertical dimension.

FIGS. 2B to 2D show different possible "closed" geometries for the nanoscale grooves 25A. The geometries of the nanoscale grooves 25A are said to be "closed" when the movement of the molecules 19 within the nanoscale grooves 25A is constrained. Stated differently, the molecules 19 are prevented from exiting each closed nanoscale groove 25A when the first substrate 21 is contacting the second substrate 22. In these "closed" geometries for the nanoscale groove 25A, the molecule 19 is trapped within the nanoscale groove 25A.

The closed geometry of the nanoscale grooves 225A in FIG. 2B is circular, forming a closed loop. The molecules 19 are trapped within the circular nanoscale grooves 225A when the first substrate 21 is contacting the second substrate 22. The circular nanoscale grooves 225A vary in diameter and are concentric. The closed geometry of the nanoscale grooves 325A in FIG. 2C is annular or ring-like. The molecules 19 are trapped within the ring nanoscale grooves 325A when the first substrate 21 is contacting the second substrate 22. The ring nanoscale grooves 325A have the same diameter and are spaced apart from each other along the surface 22A of the second substrate 22. The closed geometry of the nanoscale pits 425A in FIG. 2D is rectangular. The molecules 19 are trapped within the rectangular nanoscale pits 425A when the first substrate 21 is contacting the second substrate 22, and the molecules can fold onto themselves within the nanoscale pits 425A depending on their size. The rectangular nanoscale pits 425A have the same dimensions and are spaced apart from each other along the surface 22A of the second substrate 22. It will be appreciated that other closed geometries are possible, and include for example, a triangle and any polygon having at least five sides.

Referring to FIGS. 2A to 2D, after a sample is loaded into the fluidic chamber 24, the first substrate 21 is displaced to be pushed against the second substrate 22. This reduces the dimension of the fluidic chamber 24, causing the DNA molecules 19A to be entropically driven into the nanoscale grooves 25A depicted in FIGS. 2A to 2D. The DNA molecules 19A also feel the global confinement potential of the now curved or shrunken chamber. When using a linear or open nanoscale groove 125A, such as the ones shown in FIG. 2A, the resulting confinement gradient experienced by the linearized DNA molecules 19A causes them to drift along the linear nanoscale grooves 125A towards regions of lower confinement, and away from the optical imaging centred on the centre of the flow cell 20. The DNA molecules 19A eventually move out from the field of view over a sufficiently long timescale and from the linear nanoscale grooves 125A themselves as the separation between the first and second substrates 21,22 is increased.

In contrast, the use of the closed geometries of the nanoscale grooves 225A,325A,425A of FIGS. 2B to 2D coupled with the confinement provided by the first substrate 21 contacting the second substrate 22, the DNA molecules 19A may not exhibit biased motion along the closed nanoscale grooves 225A,325A,425A. FIG. 2E compares the molecule drift observed in an "open" linear nanoscale groove 125A with that of a "closed" ring nanoscale groove 325A. FIG. 2E depicts the fraction of the initial number of trapped DNA molecules 19A in a single field of view plotted as a function of time for both linear and ring nanoscale groove 125A,325A arrays. The closed ring nanoscale grooves 325A maintain a higher percentage of the DNA molecules 19A in view throughout the measurement period in comparison to the open linear nanoscale grooves 125A. The open linear nanoscale grooves 125A are essentially empty within about 10 minutes. In the open linear nanoscale grooves 125A, the majority of linearized DNA molecules 19A escape the linear nanoscale grooves 125A or field of view within tens of minutes. In the closed ring nanoscale grooves 325A, nearly all of the DNA molecules 19A remain within the field of view for the 1-hour observation period. It therefore appears that exploiting nanoscale structures with closed geometries supports extended observation of molecules 19 within these nanoscale structures. This prolonged control of the molecules 19 can allow for programmable control of the ambient fluidic environment around the molecules.

Referring to FIG. 2C, contact between the first substrate 21 and the second substrate 21 causes displacement of the molecules 19 into the ring nanoscale grooves 325A and confines the molecules 19 therein. The molecules 19 are therefore top-loaded into ring nanoscale grooves 325A. The surface 21A or "roof" comes into contact with the surface 22A or "floor" so that the ring nanoscale grooves 325A become effective sealed. With no place to go, the molecules 19 become linearized or "straightened-out" within the nanoscale groove 325A, and are trapped therein. The molecules 19 can therefore be observed for long periods of time, which enables extended observations, and increases the chance of observing interactions, especially for weak and slow interactions.

In the depicted embodiment where the molecules 19 are DNA molecules 19A, the circumference of the ring nanoscale groove 325A can be proportional to a length of the DNA molecule 19A. In the depicted embodiment, the circumference of the ring nanoscale grooves 325A is substantially equal to a length of a DNA molecule 19A when extended. The circumference of the ring nanoscale groove 325A can vary depending on the molecule 19 to be confined therein. In the depicted embodiment, the circumference is between 13 μm and 18 μm.

The ability to manipulate polymer molecular conformations on the nanoscale and to load them into closed geometry nanoscale structures is believed to improve self-ligation of the molecule. Self-ligation of DNA molecules 19A, for example, requires a ligase protein, which catalyzes the formation of phosphodiester bonds, to find one end of the fluctuating polymer. Simultaneously, the ligase must come into contact with the other fluctuating end of the polymer, which eventually leads to formation of a circular polymer. In three-dimensional space, the large number of conformations accessible to the DNA molecule 19A makes it unlikely for the polymer ends to find each other, reducing the efficiency of a self-ligation reaction. The closed ring geometry of the nanoscale grooves 325A helps to bring the opposed ends of the DNA molecules 19A into sufficiently close proximity with each other such that they may interact When the circumference of the ring nanoscale groove 325A is similar to a length of the DNA molecule 19A extension, within a tolerance determined by the polymer fluctuations, self-ligation may be further facilitated.

Figure 3A:
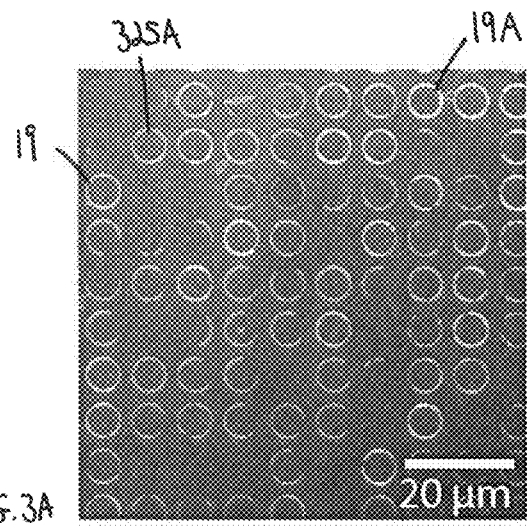
FIG. 3A shows a wide field image of molecules confined in an array of ring-shaped nanoscale grooves.
Figure 3B:
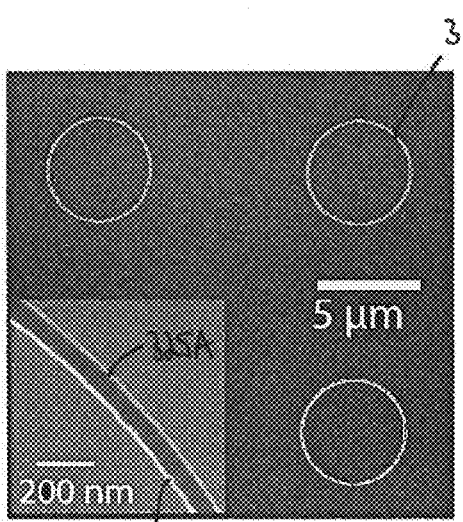
FIG. 3B shows an SEM image of a ring-shaped nanoscale groove array together with an inset of a close-up image.
Figure 3C:
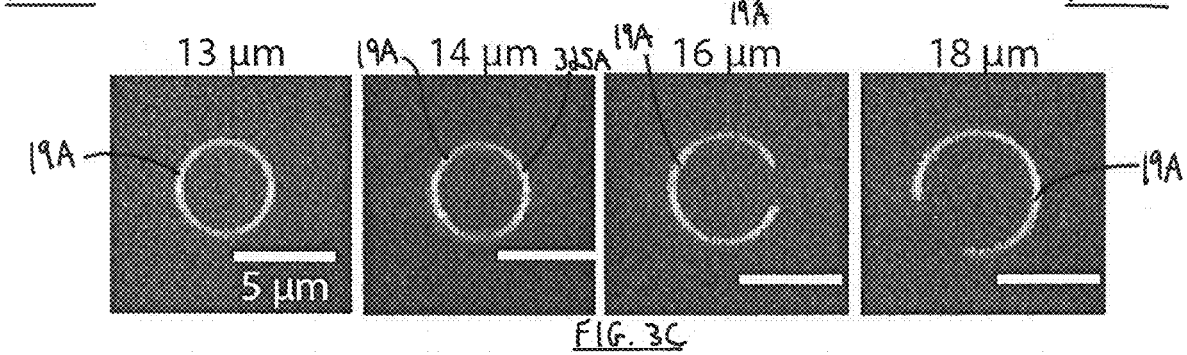
FIG. 3C shows ring-shaped nanoscale grooves having different circumferences.
Figure 3D:
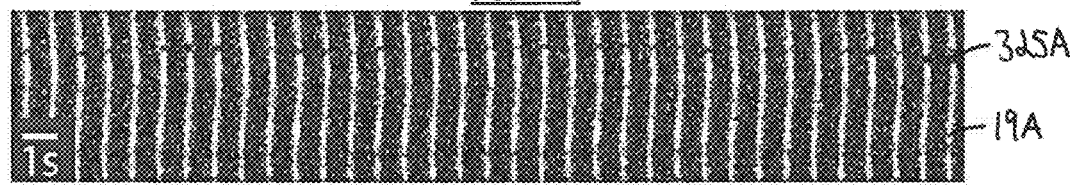
FIG. 3D shows a kymogram of a DNA molecule trapped in a ring-shaped nanoscale groove.

FIGS. 3A to 3D show DNA molecules 19A trapped within different ring nanoscale grooves 325A. FIG. 3A shows a wide field image of μ-DNA molecules 19A trapped in an array of ring nanoscale grooves 325A. FIG. 3B depicts an SEM image of a ring nanoscale groove 325A array together with an inset of a close-up image showing an approximately 70 nm width. The depth of the ring nanoscale grooves 325A is approximately 65 nm. If the ligation enzyme and required reagents are present when the ends of the DNA molecule 19A are within close proximity, self-ligation may occur. Several ring circumferences have been fabricated on a single substrate, including circumferences of 13, 14, 15, 15.5, 16, 16.5, 17, and 18 μm, of which examples are depicted in FIG. 3C with fluorescence images of the single DNA molecule 19A in the ring nanoscale grooves 325A of different sizes. When the ring circumference is shorter than the extended DNA molecule 19A, the ends of the DNA molecule 19A overlap (see, e.g. the image with the 13 μm circumference). When the circumference is larger, the ends do not meet (see, e.g., the images with the 16 μm and 18 μm circumferences). In FIG. 3C, a circumference of 14 μm was found to be suitable for ligation for the device and solution conditions used. FIG. 3D shows a kymogram of the DNA molecule 19A trapped in a 14 μm circumference ring nanoscale groove 325A, in the absence of enzyme, in which ligation is not occurring. There is a small gap between the DNA molecules 19A polymer ends which occasionally closes due to thermal fluctuations in polymer extension length. FIGS. 4A and 4B show two ligation events. Within each sequence of images in FIGS. 4A and 4B), a self-ligated DNA molecule 19A is trapped within a ring nanoscale groove 325A having 14 μm circumference shown in left to right as the first substrate 21 is slowly raised away from the second substrate 22. Accordingly, an embodiment of the nanoscale surface topography 25 disclosed herein facilitates a gentle, controlled top-loading of DNA molecules 19A into circular or ring nanoscale grooves 325A, as well as other geometries. This helps to extend observation times of the DNA molecules 19A, while establishing observation conditions free of an applied gradient or flow.

FIGS. 5A and 5B show another embodiment of the flow cell 120. The first substrate 121 includes a membrane 126. The membrane 126 in the depicted embodiment has an upper first portion 126A and a lower second portion 126B. The membrane 126 is spaced apart from the surface 121A of the first substrate 121 by supporting walls 127. The walls 127 surround an array of microfluidic chambers 127A. The microfluidic chambers 127A extend between the surface 121A and the membrane 126. The microfluidic chambers 127A are spaced apart so that they are addressable individually, both in terms of fluid exchange and in terms of electrical connection. The microfluidic chambers 127A are in communication with outlet vias 127B in the surface of the first substrate 121. The membrane 126 in the depicted embodiment enables molecules to be loaded into the individually addressable pores, between the first (top) and second (bottom) substrates 121,122. The first portion 126A of the membrane 126 has a thickness between 1-10 nm, and has multiple nanoscale pores 128 extending through the first portion 126A. The second portion 126B of the membrane 126 has a thickness of about 50 nm, and is thus thicker than the first portion 126A. The second portion 126B of the membrane has a multiple nanoscale grooves 25A etched into the second portion 126B. The nanoscale grooves 25A have a thickness of about 50 nm. The nanoscale grooves 25A are vertically aligned with the nanoscale pores 128, and in fluid communication therewith.

Referring to FIG. 5C, the membrane 126 partitions the fluidic chamber 124, when the first and second substrates 121,122 are brought into contact, into a first portion 124A having the microfluidic chambers 127A, and a second portion 124B having the nanoscale grooves 25A. The nanoscale pores 128 allow the fluid solution and molecules to be exchanged between the nanoscale grooves 25A and the microfluidic chambers 127A. In a typical implementation, molecules are confined in the nanoscale grooves 25 where they are linearized by the displacement of the second substrate 122 toward the first substrate 121, and are drawn up through the nanoscale pores 128 into the microfluidic chambers 127A for electrical sensing. The microfluidic chambers 127A are also connected to fluidics which can exchange the solution in the microfluidic chambers 127A.

The membrane 126 therefore creates a "dual-layer" fluidic chamber 124. This dual-layer configuration also allows for buffer and reagent exchange between the nanoscale grooves 25A and the microfluidic chambers 127A, once the first and second substrates 121,122 are in contact, while also providing sufficient sealing to prevent the escape of molecules trapped in the nanoscale grooves 25A. One possible use of the flow cell 120 is to deliver solution from the microfluidic chambers 127A, via the nanoscale pores 128 in the membrane 126, to the molecules which have been confined in the nanoscale grooves 25A, without disturbing the molecules which are trapped in the nanoscale grooves 25A. For example, trapped linearized molecules can be "immersed" with a solution of small-molecule reagents diffusing through the nanoscale pores 128, before they are drawn up through the nanoscale pores 128 by an applied electrical force. In an alternate embodiment, the second substrate 122 has nanoscale features as well, such as other grooves or extrusions, to change the confinement geometry.

In the depicted embodiment, the nanoscale surface topography and the nanoscale grooves 25A are on only the first substrate 121. Stated differently, the nanoscale grooves 25A are on the top of the initial liquid layer during loading of the flow cell 120. Other features can be fabricated on the second substrate 122, and may require alignment with the first substrate 121. The nanoscale grooves 25A are open-faced and patterned onto a suspended membrane 126. In the depicted embodiment, the width of nanoscale grooves 25A and nanoscale pores 128 is different The nanoscale pores 128 are positioned at one of the ends of the nanoscale grooves 25A.

Each microfluidic chamber 127A is in contact with one electrical sensor only, for example embedded directly above it There are separate decoupled outlet vias which enable fluid exchange between each microfluidic chamber 127A. Each microfluidic chamber 127A is isolated when the first and second substrates 121,122 are in contact, if closed nanoscale grooves 25A are used (e.g. ring nanoscale grooves 25A). In the depicted embodiment, each of the microfluidic chambers 127A is much bigger than the nanoscale grooves 25A. This difference in volume or width helps encourage migration of the molecules from the nanoscale grooves 25A to the microfluidic chambers 127A via the nanoscale pores 128, typically with the application of a driving force to drive the molecules through the nanoscale pores 128.

Molecules are confined in the nanoscale grooves 25A of the flow cell 120 by deflecting one or both of the first substrate 121 or the second substrate 122. In the depicted embodiment, the second substrate 121 is displaceable to contact the membrane 126 through the fluidic chamber 124, as shown in FIG. 5A. Contact between the part of the membrane 126 and the second substrate 122 causes the molecules to displace into the nanoscale grooves 25A and confines the molecules within the nanoscale grooves 25A. Any reagent or other solution can be exchanged with the confined molecules by admitting the reagent into the nanoscale grooves 25A via the nanoscale pores 128.

The molecules can also be displaced along the nanoscale grooves 25A and through the nanoscale pores 128. It is therefore possible to thread the linear or straightened molecule through the nanoscale pore 128. In the embodiment where the molecule is a charged DNA molecule, the DNA molecule can be driven along the nanoscale groove 25A and through the nanoscale pore 128 by applying a potential, bias voltage, or electric field. This causes the extended DNA molecule in the nanoscale groove 25A to be driven toward the nanoscale pores 128, and eventually threaded through them. Since the nanoscale grooves 25A confine the DNA molecules in small volumes near the nanoscale pores 128 and pre-stretch the DNA molecules and eliminate loops and folds in their conformations, only small forces may be required to thread the DNA molecules through the nanoscale pores 128. The microfluidic chambers 127A may have electrical contacts or other sensors to detect the presence of translocated DNA molecules via the nanoscale pores 128.

FIGS. 6A and 6B show another embodiment of the flow cell 220. The first substrate 221 includes a membrane 226 that is spaced apart from the surface 221A by a structure, such as by the walls 223 of an enclosed microfluidic chamber 227A. The membrane 226 is "suspended" between the fluid in the microfluidic chamber 227A and the fluid in the volume defined between the membrane 226 and the second substrate 222. When the first and second substrates 221,222 are brought into contact, the membrane 226 is "suspended" between the upper microfluidic chamber 227A and the lower nanoscale grooves 25A containing molecules and solution. The membrane 226 in the depicted embodiment is a porous body between the first and second substrates 221,222. The membrane 226 has a typical thickness between 30 and 100 nm. When the first and second substrates 221,222 are in contact, the membrane 226 partitions the fluidic chamber 224 into a first portion 224A having the microfluidic chamber 227A, and a second portion 224A having the nanoscale grooves 25A. The membrane 226 has one or more nanoscale pores 228 which extend through the membrane 226. The nanoscale pores 228 allow the fluid solution to be exchanged between the microfluidic chamber 227A and nanoscale grooves 25A of the second substrate 222.

The membrane 226 therefore creates a "dual-layer" fluidic chamber. This dual-layer configuration allows for reagent exchange between the microfluidic chamber 227A and the nanoscale grooves 25A, while also providing sufficiently sealing to prevent the escape of molecules from the nanoscale grooves 25A. One possible use of the flow cell 220 is to deliver reagents from inlet vias to the microfluidic chamber 227A, via the nanoscale pores 228 in the membrane 226, to the molecules which have been confined in the nanoscale grooves 25A without disturbing the molecules. Additional features such as nanoscale posts can be added to the surface of the membrane 226 which is in contact with the fluid, or to the second substrate 222, to change the confinement geometry further.

In the depicted embodiment, the nanoscale surface topography 25 and the nanoscale grooves 25A are on the bottom surface of the fluidic chamber 224. More particularly, the nanoscale grooves 25A extend into the surface 222A of the second substrate 222. The nanoscale grooves 25A form part of the volume of the second portion 224B of the fluidic chamber 224. Each of the nanoscale pores 228 are in fluid communication with the nanoscale grooves 25A to communicate fluid between the microfluidic chamber 227A and the inlets which lead to it, and nanoscale grooves 25A. In the depicted embodiment, the width of nanoscale grooves 25A and nanoscale pores 228 is different The microfluidic chamber 227A has an outlet via 227B in the surface of the first substrate 221. The outlet via 227A is in fluid communication with one or more of the nanoscale grooves 25A via the nanoscale pores 228. For example, multiple nanoscale grooves 25A are directly below the suspended membrane 226 in the depicted embodiment. In the depicted embodiment, the outlet via 227B and the microfluidic chamber 227A is much bigger than the nanoscale grooves 25A.

Molecules are confined in the nanoscale grooves 25A of the second substrate 222 of the flow cell 220 by deflecting either the first substrate 221 or the second substrate 222. In the depicted embodiment, the second substrate 222 is displaceable to contact the membrane 226 through the fluidic chamber 224, as shown in FIG. 6B. Contact between the part of the membrane 226 and the second substrate 222 causes the molecules to displace into the nanoscale grooves 25A in the second substrate 222 and confines the molecules within the nanoscale grooves 25A. Any reagent or other solution can be exchanged with the confined molecules by admitting the reagent into the nanoscale grooves 25A via the nanoscale pores 228. Reagents are admitted into the microfluidic chamber 227A above the nanoscale pores 228 through the outlet via 227B, and they diffuse through the nanoscale pores 228.

Referring to FIG. 1B, at least the second substrate 22 is made from glass. More particularly, the second substrate 22 is made from borosilicate glass. D263 glass has a relatively low surface roughness and index of refraction which matches that of the oil-immersion objectives. In contrast, silica substrates are a common aspect of prior art substrates. However, the refractive index of silica is not well matched to high-NA oil immersion objectives. The flow cell 20 therefore includes a thin-glass nanofluidic slit with nanoscale groove 25A arrays. It has been observed to confine molecules into nanoscale features in coverslip-thickness substrates 21,22 having a thickness in the range of 100-150 µm, in contrast to millimeter-thick fused silica devices used in some conventional devices.

The use of relatively thin D263 borosilicate glass substrates 21,22 is well-matched to high-NA oil-immersion objectives. In contrast, the refractive index of fused silica is not well-matched to oil immersion objectives resulting in spherical aberrations which reduce image quality and resolution. By replacing 0.5 mm fused silica substrates used in prior work with 0.17 mm D263 substrates 21,22, it is believed possible to replace water-immersion objectives characterized by a NA 1.0 with an oil-immersion objective with NA 1.49. Images of λ-DNA molecules 19A confined within 50×65 nm$^2$ cross-section nanoscale grooves 25A in each case are shown in FIG. 7A, demonstrating decreased aberrations and typical improvement in signal-to-background ratio. FIGS. 7A to 7E depict two examples of a DNA molecule 19A labeled with a single fluorophore 19B, namely, a λ-DNA molecule with a single Cy5-labeled oligo covalently attached to one end extended in a linear nanoscale groove 25A, as well as a mutant pUC19 plasmid labeled with a single Cy5-fluorophore, trapped in an embedded micro-pit (500 nm×2 nm). Accordingly, these depict single-fluorophore 19B imaging of biomolecules 19 extended in nanoscale surface topographies 25.

FIG. 7A depicts in the upper panels µ-DNA molecule 19A, stained with YOYO-1 19B, extended in the linear nanoscale groove 25A wherein the panel of the upper left is imaged using a 0.5 mm-thick fused silica substrate with a water-immersion objective as in the prior art, while in the panel of the upper right is imaged using a 0.17 mm-thick glass substrate 21,22 with an oil immersion objective. Also depicted in the lower panels is λ-DNA molecule 19A, end-labeled with a single Cy5 fluorophore 19B wherein the lower left hand image of a single Cy5 end-label, covalently attached to one end of the DNA molecules 19A while the lower right hand image depicts an overlaid two-color image of end-label and YOYO-1 stained DNA molecule 19A. FIG. 7B depicts a histogram of intensity for the single fluorophore image in the bottom left of FIG. 7A. FIG. 7C depicts visualization of a mutant pUC19 plasmid covalently labeled with a single Cy5 fluorophore 19B in an embedded pit wherein the top image is YOYO-1-stained mutant pUC19 plasmids, some of which are labeled with single Cy5 (middle image), while the lower image is an overlaid two-color image of the labeled plasmids trapped in pits. FIGS. 7D and 7E present histograms of intensity for images of labeled plasmids in pits as depicted in FIG. 7C upper and middle panels respectively.

Micro/nanoscale reaction wells may also enhance reactions between single-molecules by increasing the effective cross section of molecules for finding one another. Nanoscale wells may be defined by electron-beam lithography, and micro wells may be defined either with electron-beam lithography or UV photolithography. In some applications, such nanoscale wells may be etched to a depth less than 500 nm so that molecules are confined within the focal plane of the microscope objective for fluorescence visualization.

In some embodiments, the nanoscale surface topography 25 of the first substrate 21 is above the surface 21A while in other embodiments it is into the surface 21A. Similarly, in some embodiments, the nanoscale surface topography 25 of the second substrate 22 is above the surface 22A while in other embodiments it is into the surface 22A. In some embodiments they are both into or both out of their respective surfaces while in other embodiments one may be into and the other out of the surface and vice-versa. For examples, nanoscale posts 127 may be formed on both surfaces to trap the molecules, while in other embodiments, nanoscale grooves/pits 25A may be formed into both surfaces to trap the molecules.

Within the embodiments described above a nanoscale pore 128 has been described as providing an "outlet" for a material trapped, e.g. biological molecule. However, within other embodiments, the nanoscale pore 128 may be replaced by one or more other nanoscale sensors. For example, a nanoscale groove or nanoscale groove/nanoscale pore combination may be employed to direct a molecule towards the nanoscale particle wherein the local electric field is enhanced such that the "read-out" is now a Raman spectrum, frequency shift, or other detection means.

Referring to FIG. 1B, there is also disclosed a method of loading the flow cell 20. The method includes providing molecules in a fluid between spaced-apart first and second substrates 21,22. At least one of the first and second substrates 21,22 has a nanoscale surface topography 25 including at least one nanoscale groove 25A extending into said substrate 21,22. The method includes displacing the first substrate 21 toward the second substrate 22 to contact at least part of the first substrate 21 against the second substrate 22. Contact between said part of the first substrate 21 and the second substrate 22 causes displacement of the molecules in the fluid into at least one nanoscale groove 25A and confines the molecules therein.

Referring to FIG. 2C, there is also disclosed another method of loading the flow cell 20. The method includes confining a biological molecule 19,19A within a nanoscale groove 25A of the flow cell 20 such that a first end of the biological molecule 19,19A is proximate to a second end of the biological molecule 19,19A.

Reference is made now to FIGS. 8 to 13 illustrating with more details various embodiments of a flow cell in accordance with the present invention.

Figure 8:
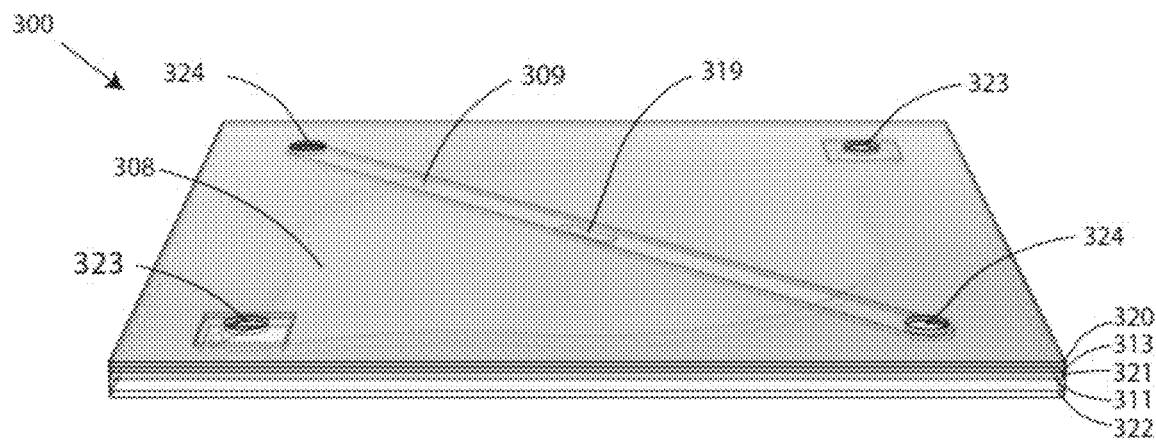
FIG. 8 is a perspective top front perspective view of a flow cell in accordance with one particular embodiment of the invention.

FIG. 8 show a flow cell 300 for confining molecules in a fluid. This particular flow cell 300 comprises an upper substrate 320, an upper support member 313, a center substrate 321, a membrane 326, a lower support member 311 and a lower substrate 322. The flow cell is provided with sample inlet/outlet 323, reagent inlet/outlet 324, a center outlet 319 comprising at least one sensing chamber 339 and an imaging chamber 308.

Figure 9:
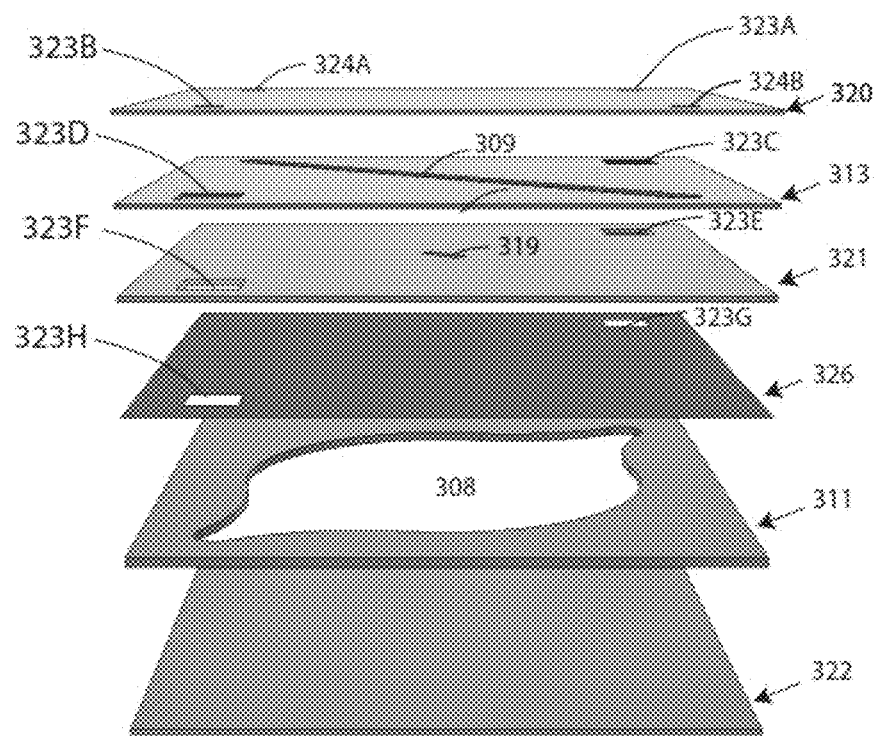
FIG. 9 is a front exploded perspective view of the flow cell FIG. 8.
Figure 10:
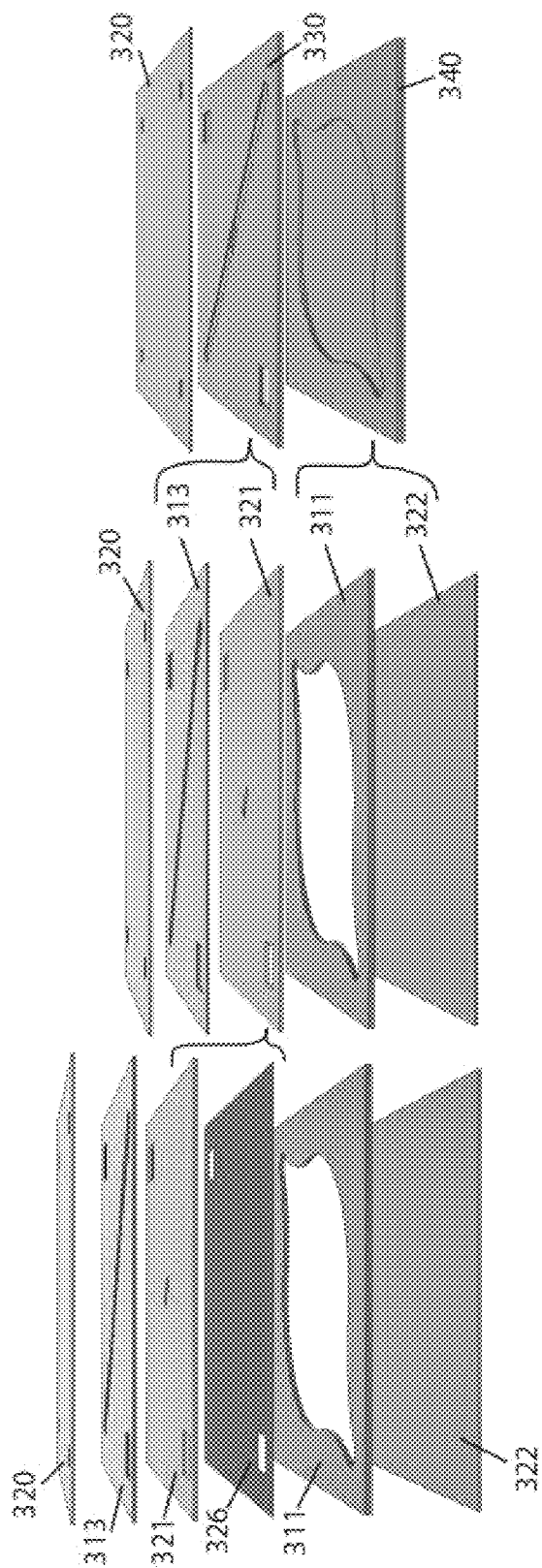
FIGS. 10A-10C are front exploded perspective views of the flow cell of FIGS. 8 and 9.

Referring now to FIG. 9, the upper substrate 320 comprises a pair of diagonally opposed sample inlet 323A and sample outlet 323B and a pair diagonally opposed reagent inlet 324A and reagent outlet 324B.

The center substrate 321 comprises a pair of diagonally opposed sample inlet 323E and sample outlet 323F vertically aligned and in fluid communication with the sample inlet 323A and sample outlet 323B of the upper substrate 320, respectively.

The upper support member 313 is positioned below the upper substrate 320 and above the center substrate 321. The upper support member 313 comprises a pair of diagonally opposed sample inlet 323C and sample outlet 323D vertically aligned and in fluid communication with the sample inlet 323E and sample outlet 323F of the center substrate 321. The sample inlet 323C and sample outlet 323D are also vertically aligned and in fluid communication with the sample inlet 323A and sample outlet 323B of the upper substrate 320. The upper support member 313 further comprises a reagent exchange chamber 309 in fluid communication with and extending in between the diagonally opposed reagent inlet 324A and reagent outlet 324B of the upper substrate 320. The reagent exchange chamber 309 is also in fluid communication with the center outlet 319 of the center substrate 321.

The membrane 326 is positioned below the center substrate 321 and above the lower substrate 322. The membrane 326 comprises a pair of diagonally opposed sample inlet 323G and sample outlet 323H vertically aligned and in fluid communication with the sample inlets 323E, 323C and 323A and the sample outlets 323F, 323D and 323B, respectively.

The lower support member 311 is positioned below the membrane 326 and above the lower substrate 322, The lower support member 311 comprises an imaging chamber 308 extending in between and in fluid communication with the diagonally opposed sample inlets 323G, 323E, 323C and 323A and the sample outlets 323H, 323F, 323D and 323B, respectively. In the illustrated embodiment the imaging chamber 308 occupies most of the surface of the lower support member 311 and it has a generally circular shape comprising a wide central section with two narrower extremities, symmetrically positioned from the center of the imaging chamber 308 which are in fluid communication with the diagonally opposed sample inlet 323G and sample outlet 323H of the membrane 326. One of the roles of the imaging chamber 308 is to receive a sample to be analysed and also to provide an empty space for allowing bending or displacement of the upper layers (i.e. 320, 313, 321, 326) of the flow cell 300, as shown in FIGS. 11B and 12B. The imaging chamber also assist in the trapping of molecules in an imaging plane, thereby allowing for long observation times and an optimized signal to noise.

There are different ways to manufacture the flow cell 300. In one embodiment, each of the upper substrate 320, upper support member 313, center substrate 321, membrane 326, lower support member 311 and lower substrate 322 consists of separate individual layers (FIGS. 9 and 10A). In another embodiment, the lower support member 311 and the lower substrate 322 consist of an integral bottom component 340 (FIGS. 10B-10C). In this embodiment the imaging chamber is etched in the integral bottom component 340, which can be made of any suitable material, including but not limited to glass (e.g. for optimal imaging conditions), such as borosilicate glass.

In another embodiment, the upper support member 313 and the center substrate 321 consist of an integral middle component 330 (FIGS. 10B-10C). In this embodiment the center outlet 319, the sample inlet 323E and the sample outlet 323F of the center substrate 321 are etched in the integral middle component 330. Likewise, the reagent exchange chamber 309, the sample inlet 323C, and sample outlet 323D of the center substrate 321 are also etched in that integral middle component 330. The integral middle component 330 can be made of any suitable material, for instance silicon. In one embodiment the middle component 330 contains a thin film of silicon (e.g. silicon nitride, silicon oxide or a combination thereof) deposited on a bottom face (i.e. face facing the lower support member 311) and that layer of silicon nitride defines the thin membrane 326 (FIGS. 10A-10C). In another embodiment the membrane 326 consists of a thin film of silicon (e.g. silicon nitride, silicon oxide or a combination thereof) deposited on a bottom face of the individual center substrate 321. In embodiments the membrane 326 has a thickness of about 10 nm to about 100 nm.

Reference is made now to FIGS. 11A to 11D showing a flow cell 300, defined herein as a "sensing device" in accordance with one particular embodiment of the invention, wherein the membrane 326 comprises perforations 329 each comprised of a nanoscale groove 428 and a nanopore 328. As best shown in the enlarged view of FIG. 11C, each perforation 329 extends through the membrane 326 and is vertically aligned and in fluidic communication with the sensing chamber 339, and it is also vertically aligned and in fluidic communication with the imaging chamber 308.

The nanoscale groove 428 has a size allowing to trap molecules to be confined therein (e.g. nucleic acid molecules such as DNA and RNA, and other long polymers) whereas the nanopore 328 has a dimension smaller than such molecules and smaller than the nanoscale groove 428. The main purpose of the nanopore 328 is to translocate trapped long molecules (e.g. polymers) across the membrane, from the imaging chamber to the sensing chamber. This is typically done for sensing applications.

In embodiments the nanoscale groove 428 has a diameter of about 5 nm to about 100 nm which is greater than the diameter of the nanopore 328 (about 2 nm to about 50 nm). The nanoscale groove 428 extends partially (e.g. about 5 nm to about 100 nm) into a lower face 327 of the membrane 326 that is facing the imaging chamber 308, whereas the nanopore 328 extends (e.g. about 5 nm to about 100 nm) into an upper face of the membrane 326 contacting the upper support member 313 to reach the nanoscale groove 428 (FIG. 11C). Therefore, the combination of the nanoscale groove 428 and nanopore 328 provides a fluid communication between the sensing chamber 339 and the imaging chamber 308.

Reference is made now to FIGS. 12A-12D showing a flow cell 300 defined herein as a "reagent exchange device" in accordance with another particular embodiment of the invention, wherein the membrane comprises a plurality of nanopores 328 and the lower substrate 322 comprises a plurality of nanoscale grooves 425. As best shown in the enlarged view of FIG. 12C, the membrane 326 comprises a plurality of perforations 329 defined as nanopores 328 extending through the membrane 326. Therefore, in this embodiment, the nanopores 328 provide a fluidic communication between the sensing chamber 339 and the imaging chamber 308.

Figure 11:
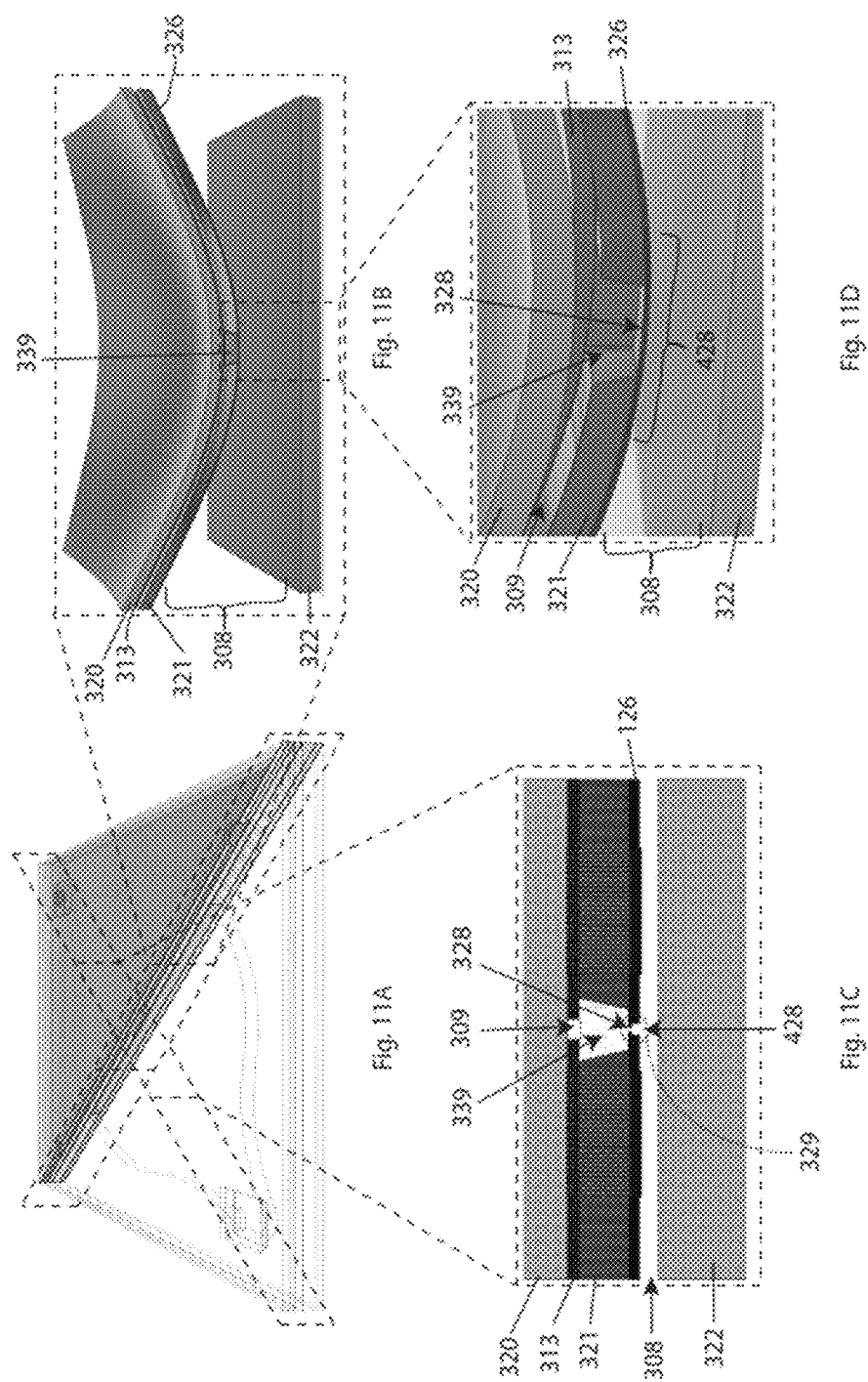
FIGS. 11A-11D is a panel of drawings of a flow cell comprising nanoscale grooves and nanopores in a membrane, in accordance with one particular embodiment of the invention.

The lower substrate 322 comprises an upper face 423 in communication with the imaging chamber 308, that upper face 423 comprising at least one (preferably a plurality of) nanoscale grooves 425 extending partially therein (e.g. about 10 nm to about 1600 nm deep), Like for the sensing device of FIG. 11, the nanoscale grooves 425 have a dimension allowing to trap molecules whereas the nanopores 328 have a dimension smaller than the molecules to be confined in the nanoscale groove(s) 425. In the reagent exchange device, the the nanopores allow for performing buffer exchange and/or additional of reagents to the trapped molecules confined in nanogrooves. This allows for visualizing reactions in real time.

In embodiments the nanoscale grooves 425 have a diameter of about 10 nm to about 50000 nm which is greater than the diameter of the nanopore 328 (about 5 nm to about 50 nm). In embodiments, the flow cell 300 comprises at least one a nanoscale groove 425 which is vertically aligned with at least one sensing chamber 339. In embodiments, a plurality of nanopores 328 are in fluid communication with each of the nanoscale groove(s) 425.

As best shown in the enlarged views of FIG. 11B and 12B, the upper substrate 320, the upper support member 313, the center substrate 321 and the membrane 326 (or the combination thereof including the upper substrate 320 and middle component 330) are displaceable (see concave shape) into the imaging chamber 308 (see reduce height in the center). Such displacement will cause molecules in the imaging chamber to be confined or trapped into the nanoscale groove(s) 425 or 428 for imaging.

Figure 12:
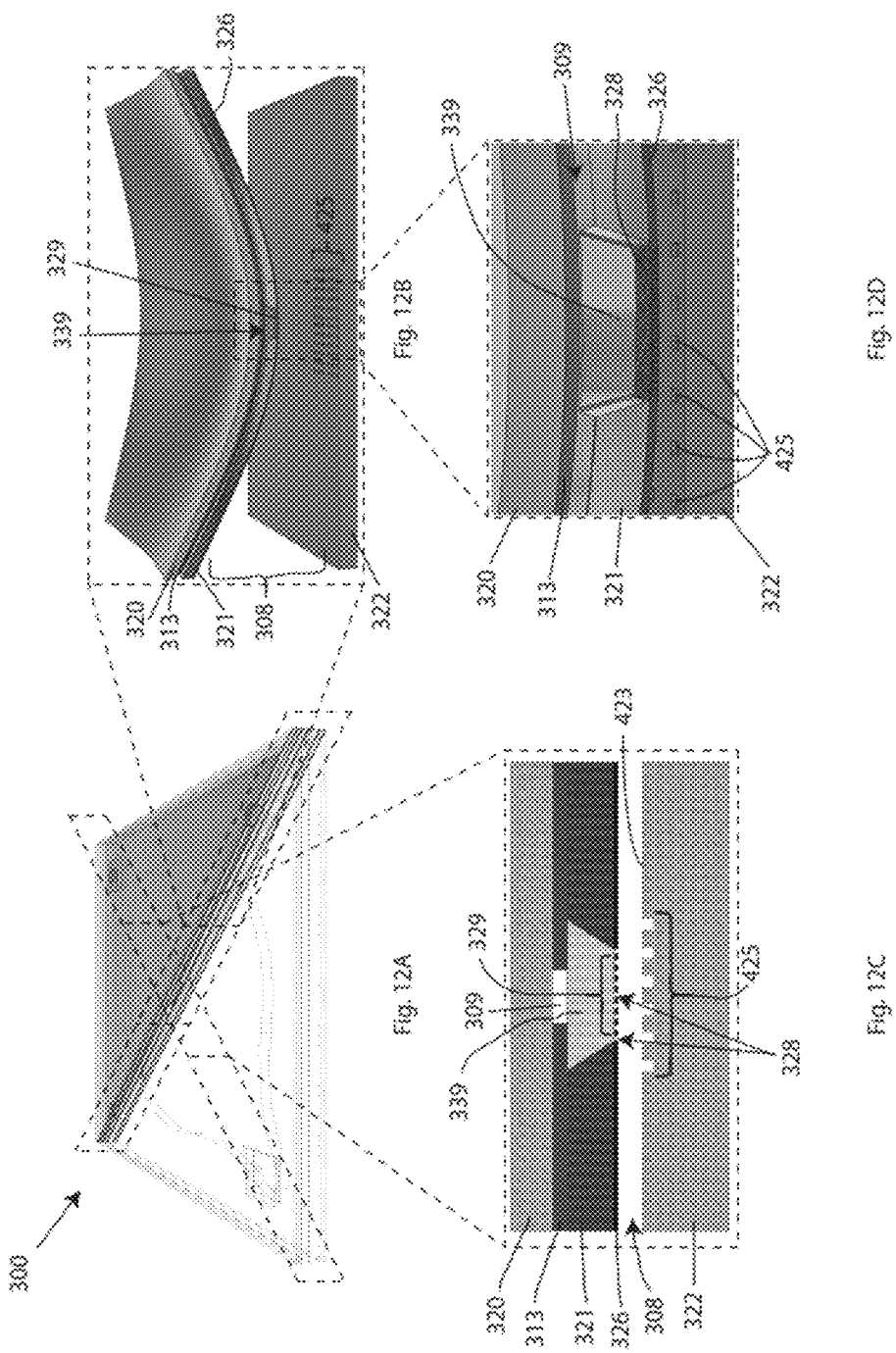
FIGS. 12A-12D is a panel of drawings of a flow cell comprising nanopores in a membrane and nanoscale grooves in a lower substrate, in accordance with one particular embodiment of the invention.
Figure 13:
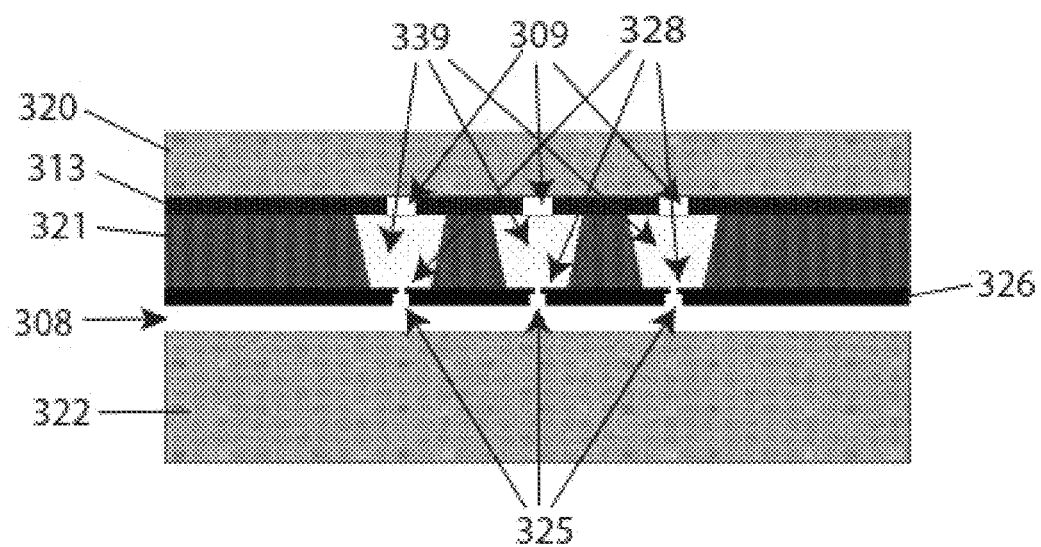
FIG. 13 is a cross-sectional enlarged view of a section of the flow cell comprising nanoscale grooves and nanopores in a membrane and comprising a plurality of sensing chambers, in accordance with another particular embodiment of the invention.

For simplicity, the flow cells 300 of FIGS. 11 and 12 are illustrated with only one sensing chamber 339. However, the center outlet 319 of flow cells 300 in accordance with the present invention preferably comprises a plurality of sensing chambers 339, as well as a plurality of associated components (e.g. corresponding perforations 329 in the membrane, etc.). For instance, FIG. 13, show a flow cell comprising a plurality of sensing chambers 339, each chamber 339 being in fluid communication with the imaging chamber 308 via a single perforation in the membrane 326 (e.g. combination of nanopore 328 and nanoscale groove 428).

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A flow cell for confining molecules in a fluid, comprising:
   an upper substrate comprising a pair of diagonally opposed sample inlet and sample outlet and a pair of diagonally opposed reagent inlet and reagent outlet;
   a center substrate comprising
      a pair of diagonally opposed sample inlet and sample outlet vertically aligned and in fluid communication with the sample inlet and sample outlet of the upper substrate, respectively; and
      a center outlet comprising at least one sensing chamber;
   a lower substrate;
   an upper support member positioned below the upper substrate and above the center substrate,
      the upper support member comprising a pair of diagonally opposed sample inlet and sample outlet vertically aligned and in fluid communication with both the sample inlet and sample outlet of the center substrate and the sample inlet and sample outlet of the upper substrate, respectively;
      the upper support member further comprising a reagent exchange chamber in fluid communication with and extending in between the diagonally opposed reagent inlet and reagent outlet of the upper substrate, the reagent exchange chamber being also in fluid communication with the center outlet of the center substrate;
   a membrane positioned below the center substrate and above the lower substrate, the membrane comprising a pair of diagonally opposed sample inlet and sample outlet vertically aligned and in fluid communication with the sample inlets and the sample outlets respectively;
   a lower support member positioned below the membrane and above the lower substrate,
      the lower support member comprising an imaging chamber extending in between and in fluid communication with the diagonally opposed sample inlets and the sample outlets.

2. The flow cell of claim 1, wherein the upper support member and the center substrate are made from silicon.

3. The flow cell of claim 1, wherein the membrane consists of a film of silicon.

4. The flow cell of claim 1,
   wherein the center outlet comprises a plurality of sensing chambers.

5. The flow cell of claim 1, wherein the membrane consists of a film of silicon deposited on a bottom face of the center substrate.

6. The flow cell of claim 1,
   wherein the membrane comprises at least one perforation extending therethrough for providing a fluidic communication between the at least one sensing chamber and the imaging chamber.

7. The flow cell of claim 1,
   wherein the membrane comprises at least one perforation comprising a nanopore and a nanoscale groove,
   wherein said at least one perforation extends through the membrane and is vertically aligned and in fluidic communication with the at least one sensing chamber, and also vertically aligned and in fluidic communication with the imaging chamber.

8. The flow cell of claim 7,
   wherein the nanoscale groove has a diameter greater than the nanopore,
   wherein the nanoscale groove extends partially through a lower face of the membrane that is facing the imaging chamber,
   wherein the nanopore extends into an upper face of the membrane and is in fluid communication the nanoscale groove.

9. The flow cell of claim 1,
wherein the center outlet comprises a plurality of sensing chambers; and
wherein the membrane comprises a plurality of perforations extending through the membrane, each perforation comprising a nanopore and a nanoscale groove providing together a fluidic communication between each of the sensing chambers with the imaging chamber.

10. The flow cell of claim 9, wherein the nanoscale groove has a shape selected from the group consisting of a circle, a ring, a rectangle, a triangle, and a polygon having five or more sides.

11. The flow cell of claim 1,
wherein the membrane comprises a plurality of nanopores extending through the membrane, the nanopores providing a fluidic communication between the at least one sensing chamber and the imaging chamber.

12. The flow cell of claim 11,
wherein the lower substrate comprises an upper face in communication with the imaging chamber,
wherein said upper face comprises a plurality of nanoscale grooves extending partially therethrough,
wherein the nanoscale grooves have a diameter greater than the nanopores and are vertically aligned with at the least one sensing chamber.

13. The flow cell of claim 12,
wherein a plurality of nanoscale grooves are in fluid communication with the imaging chamber.

14. The flow cell of claim 12, wherein the nanoscale grooves have a shape selected from the group consisting of a circle, a ring, a rectangle, a triangle, and a polygon having five or more sides.

15. A flow cell for confining molecules in a fluid, comprising:
an upper substrate comprising a pair of diagonally opposed sample inlet and sample outlet and a pair diagonally opposed reagent inlet and reagent outlet;
a center substrate comprising
a pair of diagonally opposed sample inlet and sample outlet vertically aligned and in fluid communication with the sample inlet and sample outlet of the upper substrate, respectively; and
a center outlet comprising at least one sensing chamber;
a lower substrate made from borosilicate glass;
an upper support member positioned below the upper substrate and above the center substrate,
the upper support member comprising a pair of diagonally opposed sample inlet and sample outlet vertically aligned and in fluid communication with both the sample inlet and sample outlet of the center substrate and the sample inlet and sample outlet of the upper substrate, respectively;
the upper support member further comprising a reagent exchange chamber in fluid communication with and extending in between the diagonally opposed reagent inlet and reagent outlet of the upper substrate, the reagent exchange chamber being also in fluid communication with the center outlet of the center substrate;
a membrane positioned below the center substrate and above the lower substrate, the membrane comprising a pair of diagonally opposed sample inlet and sample outlet vertically aligned and in fluid communication with the sample inlets and the sample outlets, respectively;
a lower support member made from borosilicate glass and positioned below the membrane and above the lower substrate,
the lower support member comprising an imaging chamber extending in between and in fluid communication with the diagonally opposed sample inlets and the sample outlets;
wherein the membrane comprises at least one perforation comprising a nanopore and a nanoscale groove, wherein said at least one perforation extends through the membrane and is vertically aligned and in fluidic communication with the at least one sensing chamber, and also vertically aligned and in fluidic communication with the imaging chamber;
wherein the nanoscale groove has a diameter greater than the nanopore,
wherein the nanoscale groove extends partially through a lower face of the membrane that is facing the imaging chamber, and
wherein the nanopore extends into an upper face of the membrane and is in fluid communication with the nanoscale groove.

16. A flow cell for confining molecules in a fluid, comprising:
an upper substrate comprising a pair of diagonally opposed sample inlet and sample outlet and a pair diagonally opposed reagent inlet and reagent outlet;
a center substrate comprising
a pair of diagonally opposed sample inlet and sample outlet vertically aligned and in fluid communication with the sample inlet and sample outlet of the upper substrate, respectively; and
a center outlet comprising at least one sensing chamber;
a lower substrate;
wherein the lower substrate comprises an upper face in communication with an imaging chamber,
wherein said upper face comprises a plurality of nanoscale grooves extending partially through the lower substrate, wherein the nanoscale grooves are vertically aligned and in fluid communication with the at least one sensing chamber;
an upper support member positioned below the upper substrate and above the center substrate,
the upper support member comprising a pair of diagonally opposed sample inlet and sample outlet vertically aligned and in fluid communication with both the sample inlet and sample outlet of the center substrate and the sample inlet and sample outlet of the upper substrate, respectively;
the upper support member further comprising a reagent exchange chamber in fluid communication with and extending in between the diagonally opposed reagent inlet and reagent outlet of the upper substrate, the reagent exchange chamber being also in fluid communication with the center outlet of the center substrate;
a membrane positioned below the center substrate and above the lower substrate, the membrane comprising a pair of diagonally opposed sample inlet and sample outlet vertically aligned and in fluid communication with the sample inlets and the sample outlets respectively,
wherein the membrane comprises a plurality of nanopores extending through the membrane, the nanopores providing a fluidic communication between the at least one sensing chamber and the imaging chamber;

wherein the plurality of nanopores are in fluid communication with each of the nanoscale grooves and have a diameter smaller than the diameter of the nanoscale grooves;

a lower support member positioned below the membrane and above the lower substrate, the lower support member comprising the imaging chamber, said imaging chamber extending in between and in fluid communication with the diagonally opposed sample inlets and the sample outlets.

17. A flow cell for confining molecules in a fluid, comprising:

an upper substrate comprising a pair of diagonally opposed sample inlet and sample outlet and a pair diagonally opposed reagent inlet and reagent outlet;

a center substrate comprising a pair of diagonally opposed sample inlet and sample outlet vertically aligned and in fluid communication with the sample inlet and sample outlet of the upper substrate, respectively; and a center outlet comprising at least one sensing chamber;

an integral bottom component;

an upper support member positioned below the upper substrate and above the center substrate, the upper support member comprising a pair of diagonally opposed sample inlet and sample outlet vertically aligned and in fluid communication with both the sample inlet and sample outlet of the center substrate and the sample inlet and sample outlet of the upper substrate, respectively;

the upper support member further comprising a reagent exchange chamber in fluid communication with and extending in between the diagonally opposed reagent inlet and reagent outlet of the upper substrate, the reagent exchange chamber being also in fluid communication with the center outlet of the center substrate;

a membrane positioned below the center substrate and above the integral bottom component, the membrane comprising a pair of diagonally opposed sample inlet and sample outlet vertically aligned and in fluid communication with the sample inlets and the sample outlets, and wherein the integral bottom component is positioned below the membrane, the integral bottom component comprising an imaging chamber etched therethrough, said imaging chamber extending in between and in fluid communication with the diagonally opposed sample inlets and the sample outlets.

18. The flow cell of claim 17, wherein the bottom component is made from borosilicate glass.

* * * * *